United States Patent
Rao et al.

(10) Patent No.: US 6,563,585 B1
(45) Date of Patent: May 13, 2003

(54) RATIOMETRIC FLUOROMETER

(75) Inventors: Govind Rao, Columbia, MD (US); Yordan Kostov, Baltimore, MD (US)

(73) Assignees: University of Maryland Biotechnology Institute, Baltimore, MD (US); University of Maryland, Baltimore County, Baltimore, MD (US)

( * ) Notice: Subject to any disclaimer, the term of this patent is extended or adjusted under 35 U.S.C. 154(b) by 0 days.

(21) Appl. No.: 09/449,671

(22) Filed: Nov. 30, 1999

Related U.S. Application Data

(60) Provisional application No. 60/167,238, filed on Nov. 24, 1999.

(51) Int. Cl.[7] ............................................. G01N 21/00
(52) U.S. Cl. ........................ 356/436; 356/432; 356/39
(58) Field of Search ................................ 356/436, 432, 356/433, 39, 40, 41, 311, 317, 319, 320; 128/633, 664, 665; 250/343, 341

(56) References Cited

U.S. PATENT DOCUMENTS

| | | | | |
|---|---|---|---|---|
| 3,255,355 | A | 6/1966 | Frenk et al. | 250/204 |
| 3,561,845 | A | 2/1971 | Boronkay et al. | 356/205 |
| 3,804,535 | A | 4/1974 | Rodriguez | 356/217 |
| 3,892,490 | A | 7/1975 | Uetsuki et al. | 356/161 |
| 3,892,492 | A | 7/1975 | Eichenberger | 356/199 |
| 3,910,701 | A | 10/1975 | Henderson et al. | 356/39 |
| 4,080,076 | A | 3/1978 | Carr | 356/208 |
| 4,213,462 | A | 7/1980 | Sato | 128/634 |
| 4,283,142 | A | 8/1981 | De Steur et al. | 356/319 |
| 4,305,659 | A | 12/1981 | Bilstad et al. | 356/40 |
| 4,398,541 | A | 8/1983 | Pugliese | 128/665 |
| 4,479,499 | A | 10/1984 | Alfano | 128/665 |
| RE31,815 | E | 1/1985 | Alfano | 128/665 |
| 4,616,657 | A | 10/1986 | Stoller | 128/664 |
| 4,803,049 | A | 2/1989 | Hirschfeld et al. | 422/58 |
| 4,819,646 | A * | 4/1989 | Cheung et al. | 356/41 |
| 4,836,206 | A | 6/1989 | Maxwell et al. | 128/633 |
| 4,877,034 | A | 10/1989 | Atkins et al. | 128/664 |
| 5,070,874 | A * | 12/1991 | Barnes et al. | 356/39 |
| 5,086,229 | A * | 2/1992 | Rosenthal et al. | 250/341 |
| 5,102,625 | A * | 4/1992 | Milo | 422/82.07 |
| 5,103,829 | A | 4/1992 | Suzuki et al. | 128/633 |
| 5,131,398 | A | 7/1992 | Alfano et al. | 128/665 |
| 5,212,386 | A * | 5/1993 | Gratton et al. | 356/317 |
| 5,222,495 | A | 6/1993 | Clarke et al. | 128/633 |
| 5,246,002 | A | 9/1993 | Prosser | 128/633 |
| 5,348,018 | A | 9/1994 | Alfano et al. | 128/665 |
| 5,365,559 | A * | 11/1994 | Hsueh et al. | 356/40 |
| 5,377,676 | A | 1/1995 | Vari et al. | 128/634 |
| 5,567,869 | A | 10/1996 | Hauch et al. | 73/64.41 |
| 5,818,598 | A | 10/1998 | Kebabian | 356/434 |
| 6,070,093 | A * | 5/2000 | Oosta et al. | 600/316 |

OTHER PUBLICATIONS

Author: Yordan Kostov; Govind Rao; Kelly A. Van Houston; Peter Harms; Robert Pilato Title: A Unique Oxygen Analyzer Combining a Dual Emission Probe and a Low–Cost Solid–State Ratiometric Fluorometer.Date: Sep. 1999.

Author: Yordan Kostov;Govind Rao Title:Low–cost Device for Ratiometric Fluorescence Measurements Date: Dec. 1999.

* cited by examiner

*Primary Examiner*—Hoa Q. Pham
*Assistant Examiner*—Sang H. Nguyen
(74) *Attorney, Agent, or Firm*—Sughrue Mion, PLLC

(57) ABSTRACT

A method and apparatus for measuring the concentration of various analytes in a sample using native fluorescence is described. A first light source for producing a first light having a first wavelength is directed at the sample to produce a first emission from the sample, a second light source for producing a second light having a second wavelength is directed at the sample to produce a second emission from the sample. A detecting device for detecting the first and second emissions emitted from the sample, and a controlling device responsive to the detecting device for alternately switching between the first and second light source so that only one light source is directing light at the sample at any one time are employed to excite emissions from the sample to be analyzed. An analyzing device that is responsive to the controlling device for producing a duty ratio is used to determine the analytic concentration of the specific analyte present in the sample.

27 Claims, 4 Drawing Sheets

RATIOMETRIC FLUOROMETER

REFERENCE TO RELATED APPLICATIONS

The instant application claims the benefit of U.S. Provisional Application (Ser. No. 60/167,238) filed on Nov. 24, 1999, incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of contract No. RR-10955 and contract No. RR-14170 awarded by the National Institutes of Health (NIH).

FIELD OF THE INVENTION

The present invention relates generally to an analytic apparatus and particularly to a ratiometric fluorometer for measuring the concentration of various analytes in a sample.

BACKGROUND

Currently, the predominant technique for measuring dissolved oxygen in a sample is a polarographic method involving the monitoring of the modified Clark electrode. This approach involves a relatively expensive, inefficient, and inaccurate method of measuring oxygen concentrations. In particular, the Clark electrode method is adversely affected by signal drift which in turn affects the long term stability of the electrode. Furthermore, this method is adversely affected by flow rates as a result of the electrode consuming amounts of the oxygen to be analyzed and thus causing the measurements of the oxygen concentration to be unreliable at best. Finally, while the Clark electrode method is a long-standing polarographic approach for measuring dissolved oxygen, practitioners find this method is susceptible to electrical interference that adversely affects the accuracy of the oxygen concentration measurements.

Recently, optical methods in measuring the oxygen concentration of a sample have been employed in an attempt to overcome the limitations of the Clark electrode. These optical techniques attempt to measure the oxygen induced changes in the emission intensity of a sample to determine the oxygen concentration in that sample. Optical measurement techniques are based on the premise that long-lived states of many emissive transition metal complexes (emissive dyes) are quenched at oxygen concentrations of environmental, industrial, and biomedical interest. Emissive dyes, once polymer encapsulated or dissolved in the media being analyzed, can be used to measure oxygen in the gas phase as well as in an aqueous or biomedia form. These emissive dyes include several tris(diimine)ruthenium (II) complexes and metalloporphyrins that, once polymer encapsulated or dissolved in the media under investigation, may be used for oxygen measurement. However, systems emphasizing oxygen induced changes in emission intensity have incurred various problems that have resulted in inaccurate measurements of oxygen concentration of the sample and therefore unreliable results. Measurements obtained by such systems are adversely affected by changes in optical clarity, fluctuations in the source detector, and photobleaching of the emitter. These non-analyte induced variations in emission intensity of the sample require a relatively expensive and extremely complex system that continuously restandardizes intensity based sensors in an attempt to obtain accurate measurements.

A second technique used to measure oxygen concentration in a sample utilizes a frequency modulated excitation to irradiate the sample. Use of a system embodying a frequency modulated excitation apparatus enables a lifetime dependent phase-shift to be used to measure quenching of a long-lived emissive state and thereby obtain the oxygen concentration. Although a frequency modulated phase-based method may be used to eliminate many of the problems associated with emission intensity techniques, the implementation of such methods based on frequency modulation requires an extremely expensive and complex system.

A third technique used to measure the oxygen concentration of a sample utilizes a two-dye method. An optical device is used to measure the emission intensity of both dyes and obtain an intensity ratio used to measure the oxygen concentration of the sample. Unfortunately, systems utilizing the two-dye method are adversely affected by photobleaching of one or both dyes. This non-analyte induced variation in intensity leads to gross miscalculations of the intensity ratio and results in inaccurate oxygen concentration measurements.

In addition to oxygen concentration measurements, optical methods have been employed to measure pH, $Ca^{2+}$, $Mg^{2+}$, $Zn^{2+}$, heavy metals and transmembrane potentials of samples which are very important in the biomedical field. Currently, conventional steady-state methods are used to determine these types of measurements. However, steady-state systems embodying optical measurement techniques are prone to errors due to losses in the optical path, photobleaching, scattering, and background light. Furthermore, many conventional measurement systems employ techniques that require electrical contact with the object under investigation in order for a measurement to be obtained. Frequent recalibration is needed due to such non-analyte induced variations in emission intensity of the sample. As a result of these problems and limitations, very strict experimental conditions need to be upheld during the measurement process resulting in complex measurement systems and an expensive and inefficient process that yields error-prone results.

The publication entitled "A Unique Analyzer Combining a Dual Emission Probe and a Low-Cost Solid State Ratiometric Fluorometer", with a publication date of September 1999, by Yordan Kostov, Kelly A. Van Houten, Peter Harms, Robert S. Pilato, and Govind Rao, is hereby incorporated by reference. In addition, the publication entitled "Low-cost Device for Ratiometric Fluorescence Measurements", with a publication date of December 1999, by Yordan Kostov and Govind Rao, is hereby incorporated by reference.

For example, U.S. Pat. No. 3,804,535, issued Apr. 16, 1974 to Rodriguez, the disclosure of which is hereby incorporated by reference, discloses a dual wavelength photometer apparatus for measuring an analyte in a sample. The measurement of an oxygenation characteristic of a blood sample is described as a typical use of the apparatus. Light sources are sequentially directed through a sample of blood at a predetermined recurring rate and the difference in intensity of the emerging resultant beams (called the reference light beam and measure light beam) is measured. The only light beam affected by the oxygenation of the blood sample is the measure light beam allowing the oxygen content of the blood sample to be measured. However, measuring an analyte of a sample by measuring the difference in intensity has proven to be a problematic and unreliable method. As discussed above, such intensity based measurements are adversely affected by changes in optical clarity due to losses in the optical path between the reference and measurement light sources and the photometer, photobleaching, scattering and background light, and fluctuations in the source and detector. Moreover, these non-analyte induced variations in intensity make continual restandardization of the intensity based circuit shown in FIG. 1 of the '535 Patent a requirement.

Such an instrument is described in U.S. Pat. No. 4,803,049 issued to Hirschfeld et al., the disclosure of which is hereby incorporated herein by reference. Patent No. '049 discloses a pH-sensitive optrode (optrode) for monitoring the pH of a sample of physiological fluids, such as blood. An organic dye that fluoresces when excited by a light having a particular wavelength and whose fluorescence emission intensity varies with the levels of pH in physiological fluids, such as blood, is utilized to generate a fluorescent signal used to measure the pH of a blood sample. The organic dye molecules are covalently attached to a support material that in turn is in contact with the blood sample. When illuminated, the organic dye disposed on the support is caused to fluoresce. The intensity of the organic dye fluorescence varies with the levels of pH of the blood sample. However, as discussed above, this intensity based method of pH measurement is adversely affected by changes in optical clarity due to losses in the optical path between the support material and the photomultiplier tube, scattering and background light, and fluctuations in the source and detector. Moreover, photobleaching of the dye leads to gross changes in the fluorescence intensity of the dye resulting in unreliable and inaccurate pH measurements.

For the foregoing reasons, there is a need for an apparatus that can accurately and inexpensively measure the concentrations of oxygen, pH, $Ca^{2+}$, $Mg^{2+}$, $Zn^{2+}$, heavy metals and transmembrane potentials in a sample.

SUMMARY

It is an object of this present invention to provide new and improved techniques for measuring various analytes of a sample.

It is yet another object of this invention to provide an analytic apparatus for accurately, non-invasively, quickly and continuously measuring various analytes of a sample.

It is still another object of this invention to provide an analytic apparatus for measuring various analytes of a sample using native fluorescence.

It is a further object of this invention to provide an analytic apparatus for measuring various analytes of a sample that does not require electrical contact with the sample under investigation.

It is still a further object of this invention to provide an analytic apparatus for measuring various analytes of a sample to obtain equilibrium measurements.

It is still a further object of this invention to provide a low-cost, relatively simple analytic apparatus for measuring various analytes of a sample that does not require recalibration and constant upgrades in parts and equipment.

It is still yet another object of this invention to provide an analytic apparatus for measuring various analytes of a sample that utilizes an internal reference that negates non-analyte induced intensity changes in the sample.

An analytic apparatus is disclosed for determining various analytes of a sample according to the teachings of this invention. According to one embodiment of the invention, the analytic apparatus includes a first light source for producing a first light having a first wavelength that is directed at the sample to produce a first emission from the sample, a second light source for producing a second light having a second wavelength that is directed at the sample to produce a second emission from the sample, a detecting device for detecting the first and second emissions emitted from the sample, a controlling device responsive to the detecting device for alternately switching between the first and second light source so that only one light source is directing light at the sample at any one time, and an analyzing device that is responsive to the controlling device for producing a duty ratio which is used to determine the analytic concentration of the sample.

The foregoing and other objects and advantages will appear from the description to follow. In the description, reference is made to the accompanying drawing which forms a part thereof, and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

These and other features, aspects, and advantages of the present invention will become better understood with regard to the following description, appended claims, and accompanying drawings in which:

DETAILED DESCRIPTION

Figure 1:
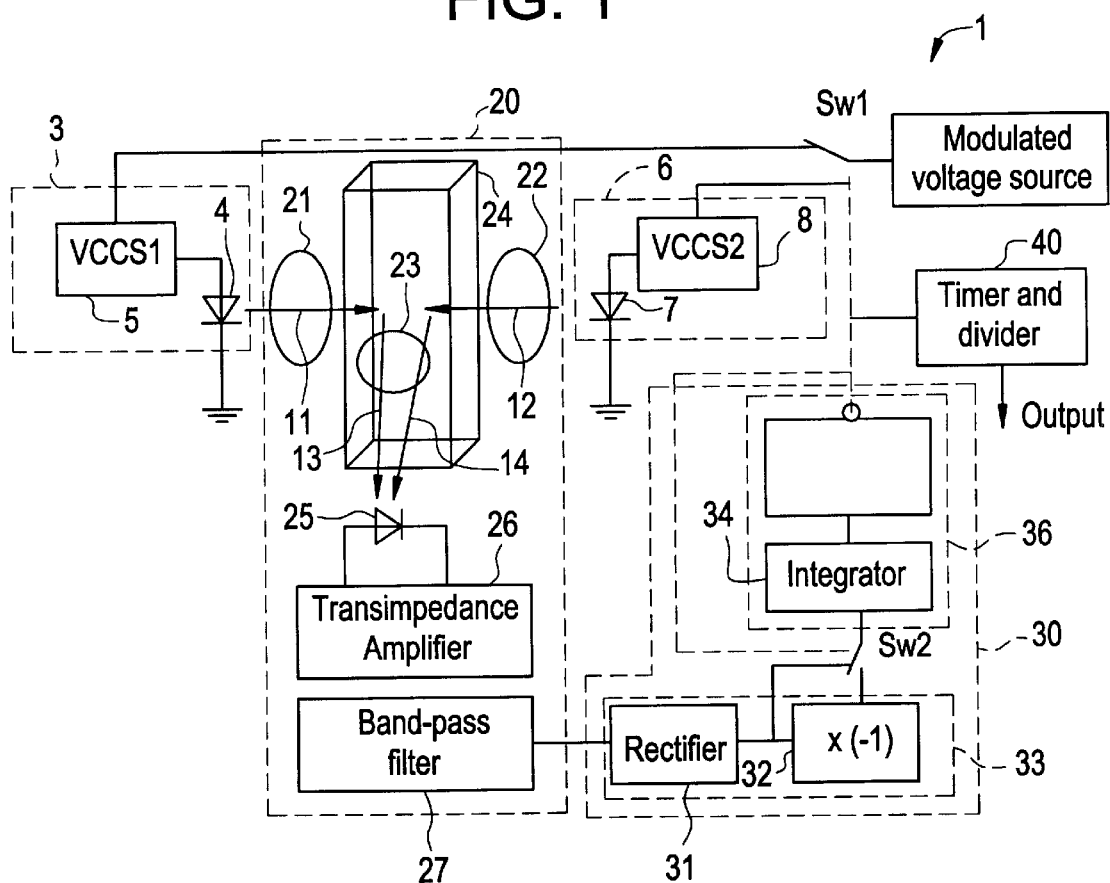
FIG. 1 is a schematic block diagram of an analytic apparatus according to one embodiment of the present invention.

The present invention is directed to a new apparatus for measuring various analytes in a sample. This apparatus is based on the above noted discovery that certain luminescent dyes have dual-emitting characteristics when dissolved in room temperature solutions or when polymer encapsulated, and when excited by modulated light.

The present invention is based on the apparatus and method that enables various analytes in the sample to be measured either by utilizing: (1) a dual-excitation probe comprising a dual-excitation indicator in solution or polymer-encapsulated; or (2) a dual-emission probe comprising a dual-emission dye in solution or polymer-encapsulated. The dual excitation probe posses at least two maximum in its excitation spectrum. The dual emission probe possess at least two peaks in their emission spectrum. The emission peaks may be both fluorescent emissions or fluorescent and phosphorescent emissions. It should be understood that when the probe is in contact with the analyte, the amplitude of one of these peaks is affected—either because of the changes in the electron structure of the dye or because of dynamic quenching. These fluorescent and phosphorescent emissions are measured in one embodiment of the present invention and used to measure the analyte of the sample. In the present invention, the duty ratio of the hysteresis trigger 35 (T1/T2) is proportional to the luminescence intensity ratio. The period of the square wave (T1+T2)—the illumination cycle time—is proportional to the concentration of the emissive dye (fluorophor) used in the sample.

As a pH analyzer, the analytic apparatus of the present invention is configured to measure fluorescence emissions of indicator solutions made up of dual-excitation dyes so that the pH concentration of a sample may be measured. A pH sensitive carboxydichlorofluororescein may be used in the present invention as a dual excitation indicator to measure the pH level of a sample. In a preferred embodiment, a 5-(and 6-)-carboxy-2'7'-dichlorofluorescein, mixed isomers (5-(and 6-CDFC)), pKa 3.8, is used as a dual-excitation indicator for measuring the pH of a sample.

As an oxygen analyzer, the analytic apparatus of the present invention is configured to measure the relative fluorescence and phosphorescence intensity of the short-lived singlet and long-lived oxygen-quenchable triplet of [(dppe)Pt$\{S_2C_2(CH_2CH_2$—N-2-pyridinium)$\}$][$BPh_4$], where dppe is 1,2-bis(diphenylphosphino)ethane, a dual-emission dye. The analytic apparatus may also be configured to measure other dual emission-dyes such as several carboxy SNAFL-1 and carboxy SNAFL-2 dyes, as well as SNARF-1 and SNARF-2 dyes, when these dual-emitting dyes or molecular probes are polymer encapsulated, or dissolved in the media being analyzed.

The present invention includes a sensing dye that is a heterocyclic-substituted platinum-1,2-enedithiolate, $L_2Pt\{S_2C_2$(Heterocycle)(R)$\}$. This new class of luminescent molecules is both fluorescent and phosphorescent in room temperature solutions and when polymer encapsulated or dissolved in solution. The two emissions, fluorescence and phosphorescence, are assigned to an intraligand charge-transfer singlet, ($^1$ILCT*), and triplet, ($^3$ILCT*) with considerable 1,2-enedithiolate π to heterocycle π* character. The quantum yields and lifetimes of these complexes in room temperature solutions vary with the heterocycle, the ancillary $L_2$-group, the R-group, and solvent polarity. As a class of molecules, the solution lifetimes of the singlet are generally less than 1 ns while the triplet lifetimes vary from 1–16 µs. All of the emissive dye molecules in this family have an excitation maximum near 470 nm, making them compatible with the analytic apparatus described herein.

In a preferred embodiment, the [(dppe)Pt$\{S_2C_2$(CH$_2$CH$_2$—N-2-pyridinium)$\}$][$BPh_4$] dye molecule is immobilized in cellulose acetate (CA) which contains 75% by weight triethylcitrate (TEC), where the TEC percentage is based upon the weight of CA and is used to plasticize the polymer. The lumiphore loading is 0 3% of the combined CA/TEC weight. It is well understood by those skilled in the art that the sensitivity of polymer immobilized lumiphores to oxygen quenching is controlled, by a large extent, by the polymer and plasticizer content. In the preferred embodiment, the CA/75% TEC polymer is utilized because of the stability of the polymer when cast into films, and the compatibility of the polymer with certain preferred oxygen concentrations and pressures.

Excitation of the [(dppe)Pt$\{S_2C_2(CH_2CH_2$—N-2-pyridinium)$\}$][$BPh_4$] dye molecule in CA75% TEC under $N_2$ results in the dual-emission characteristics of this family of complexes. The singlet and triplet maximum are at 560 and 675 nm, respectively, and the triplet/singlet ratio under $N_2$ is ≈1.03. The selective loss of the $^3$ILCT* emission in air results in a drop of the triplet/singlet ratio to 0.62. Excitation under $O_2$ results in nearly a complete loss of the $^3$ILCT* emission. While the average $^3$ILCT* lifetime under $N_2$ is 14 µs, it decreases to 4.6 µs in air. A phase shift decrease of greater than 20° at 50,000 Hz accompanies the decrease in lifetime. Both observations are consistent with oxygen quenching of the $^3$ILCT*.

Furthermore, the triplet state of these dual-emitting dyes can be selectively quenched by a number of electron, proton, hydrogen atom and energy transfer processes allowing for the measurement of a range of analytes such as pH, $Ca^{2+}$, $Mg^{2+}$, $Zn^{2+}$, heavy metals and/or transmembrane potentials, to include a few.

The relative phosphorescence/fluorescence or fluorescence/fluorescence or phosphorescence/phosphorescence intensity ratios may be used in the present invention to measure a range of analytes present in a sample. The concentration of the analytes to be measured determines the emission intensities of the fluorophor and thus the luminescence intensity ratio. Therefore, the differences in spectra can be used to measure analytes in any number of ways. In one embodiment of the present invention, the analytic apparatus measures the ratio of two different samples. In another embodiment of the present invention, the analytic apparatus measures the ratio of intensity when one sample is excited on two different wavelengths. As still another embodiment of the present invention, the analytic apparatus measures the ratio of the emissions on two different wavelengths.

Referring now to FIG. 1, a diagram of an analytic apparatus according a preferred embodiment of the present invention is shown. Analytic apparatus 1 includes a first light source 3, a second light source 6, a controller 30 for controlling the first and second light sources, an emission detector 20 (detector) and an analyte analyzer 40 (analyzer), all interconnected using circuitry commonly known to those skilled in the art.

The first light source 3 includes a LED 4 which produces a first excitation light 11 at a first wavelength. The first light source 3 is coupled to a first voltage controlled current source 5. Similarly, the second light source 6 includes a LED 7 which produces a second excitation light 12 at a second wavelength, wherein the second light source 6 is coupled to a second voltage. controlled current source 8. The first excitation light 11 has a wavelength configured to excite a fluorescence emission 13 in the sample when the sample is irradiated by the first excitation light 11. The second excitation light 12 has a wavelength configured to excite a fluorescence emission 14 in the sample when the sample is irradiated by the second excitation light 12.

Emission detector 20 is configured to sequentially detect the fluorescence emission 13 and the fluorescence emission 14 emitted from the sample. The emission detector 20 converts the emitted fluorescence 13 and the emitted fluorescence 14 into electrical signals corresponding to the luminescence intensity of both fluorescence emissions and transfers, via an electrical coupling, the converted signals to the analyzer 40. Analyzer 40 processes the electrical signals and derives a luminescence duty ratio (described below) for at least one cycle of fluorescent emissions. Analyzer 40 then compares the calculated ratio with predetermined values to determine the concentration of the analyte in the sample.

Figure 2A:
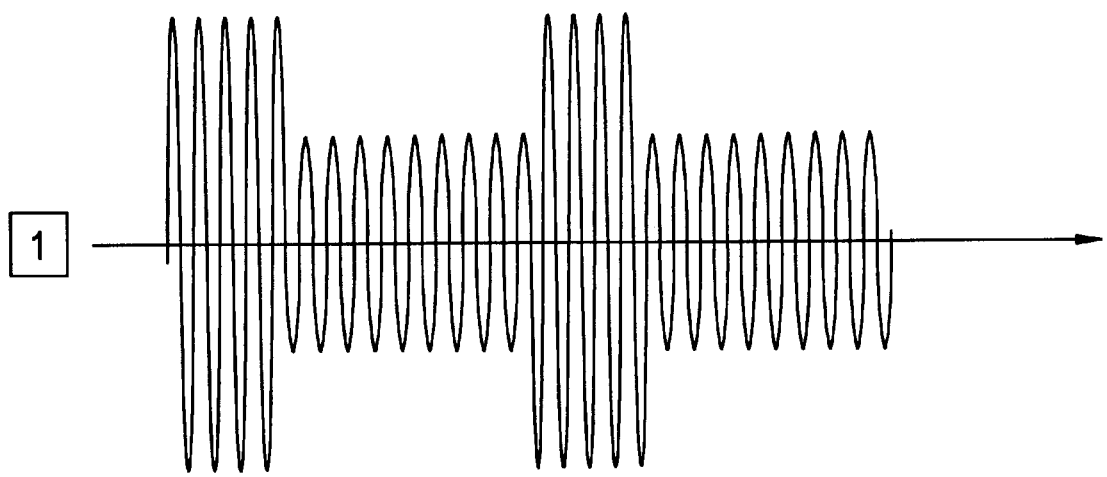
FIG. 2a is a chart illustrating the output of the emission detector according to one embodiment of the present invention.

As shown in FIG. 1, the emission detector 20 preferably includes a translucent cuvette or a like container 24 having an internal dimension for holding a sample to be illuminated, a first excitation filter 21 for filtering the excitation light 11 produced by the LED 4, and a second excitation filter 22 for filtering the excitation light 12 produced by the LED 7. It should be understood that the cuvette 24 is described to facilitate understanding of the present invention, and does not form a part thereof. Any vessel performing the functions described herein may be used with the analytic apparatus 1 without departing from the scope of the present invention. A photodetector 25 converts the fluorescence emissions emitted by the sample to corresponding electrical signals. An emission filter 23 disposed intermediate the sample and the photodetector 25 is utilized to monitor the fluorescence emissions. The electrical signals corresponding to the fluorescent emissions are amplified by a transimpedance amplifier 26 and passed through a band-pass filter 27 that both (i) removes steady-state components which originate from ambient light that enters the optical path of the fluorescent emissions detected by the photodetector 25, and (ii) diminishes the level of the low and high frequency noise that accompanies the fluorescent emissions. The outputs of the band-pass filter 27 are shown in FIG. 2a.

With reference to FIG. 1, the analytic apparatus 1 also includes the controller 30 that controls the illumination cycle of the analytic apparatus 1 by alternating the first light source 3 and the second light source 6 in response to the electrical signals produced by the emission detector 20. Controller 30 includes an amplitude detector 33, for taking the absolute value of the electrical signals produced by the emission detector 20 and assigning a sign to the one of the electrical signals corresponding to one of the fluorescent emissions. The controller 30 further includes a voltage analyzer 36 that controls a pair of switches SW1 and SW2, in response to the electrical signals output by the emission detector 20, that both enable the first light source 3 and the second light source 6 to operate in a sequential manner and direct the amplitude detector 33 to assign a negative value to the amplitude of one of the electrical signals corresponding to one of the fluorescent emissions.

Figure 2B:
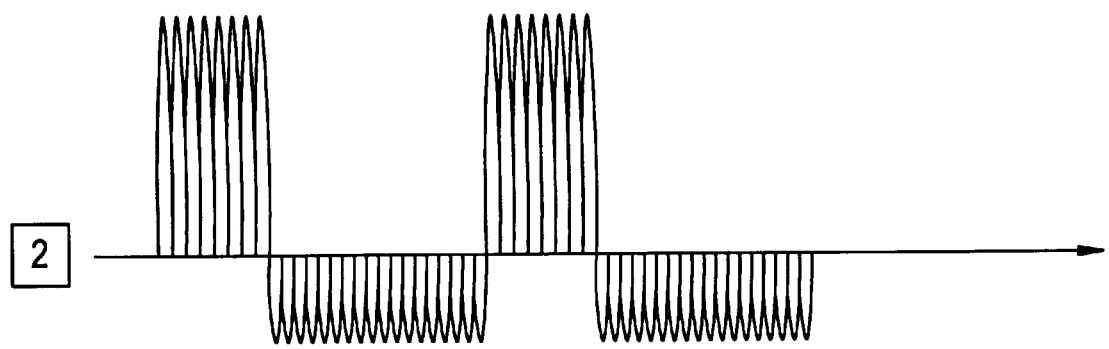
FIG. 2b is a chart illustrating the output of the amplitude detector according to one embodiment of the present invention.

As can be seen from FIG. 1, the amplitude detector 33 includes a rectifier 31 and a multiplier 32. The rectifier 31 detects the amplitude of the electrical signals corresponding to the fluorescent signals produced by the emission detector 20. One of the electrical signals corresponding to the fluorescent emissions is transmitted to the multiplier 32 via the switch SW2 that is activated by the voltage analyzer 36. In a preferred embodiment, the amplitude of the electrical signal corresponding to the second fluorescence emission is assigned a negative value by transmitting that signal through the multiplier 32. Multiplier 32, in turn, converts the positive amplitude of the second fluorescence signal output by the rectifier 31 to a negative amplitude by multiplying the first fluorescence signal by (−1). Alternatively, the electrical signal corresponding to the first fluorescence emission may be assigned a negative amplitude while the amplitude of the electrical signal corresponding to the second fluorescence emission may remain positive. The outputs of the amplitude detector are shown in FIG. 2b.

Figure 2C:
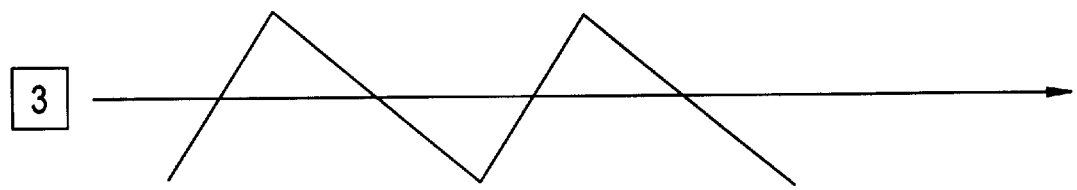
FIG. 2c is a chart illustrating the output of the voltage analyzer according to one embodiment of the present invention.
Figure 2D:
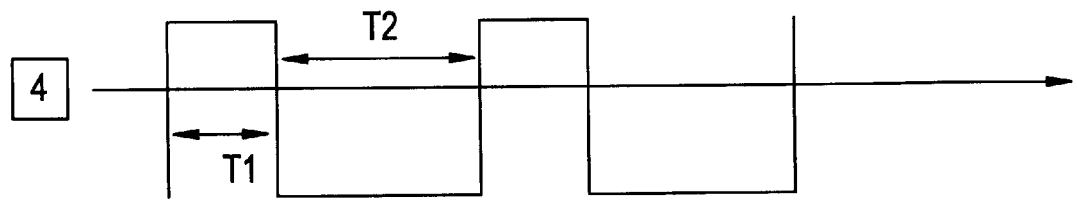
FIG. 2d is a chart illustrating the output of the hysteresis trigger according to one embodiment of the present invention.

Referring to FIG. 1 again, the voltage analyzer 36 includes an integrator 34 for integrating the electrical signals corresponding to the fluorescence emissions output by the amplitude detector 33, and a trigger 35 with hysteresis (hysteresis trigger) for directing the switches SW1 and SW2 in response to the output of the integrator 34, to enable one of the light sources and enable or disable the multiplier 32, respectively. As a result, the output of the hysteresis trigger 35 is a square wave, as can be seen in FIG. 2d. The time T1 illustrates the time that the first light source 3 is on for part of the illumination cycle. The time T2 illustrates the time that the second light source 6 is on during the remainder of the illumination cycle. Analyzer 40 computes the output of the trigger 35 to measure the duty ratio of hysteresis trigger 35 and the period of the square wave output by the hysteresis trigger 35. Analyzer 40 includes a timer 41 and divider 42 for measuring the duty ratio and the period of the hysteresis trigger 35. The analyzer 40 will be described in detail below.

As discussed above, the duty ratio of the hysteresis trigger 35 is measured by the analyzer 40 having the timer 41 and divider 42. The current that flows through the integrator 34 during an illumination cycle, equal to a half period of the modulating frequency, is given by the following equations:

$$I_1 = \int_0^{1/2f} I_{F1} \cdot \sin 2\pi ft \cdot dt, \quad I_2 = -\int_0^{1/2f} I_{F2} \cdot \sin 2\pi ft \cdot dt, \text{ or} \quad (1, 2)$$

$$I_1 = \frac{2}{\pi} I_{F1}, \quad I_2 = -\frac{2}{\pi} I_{F2}, \quad (3, 4)$$

where f is the modulation frequency of the excitation light, and $I_{F1}$ and $I_{F2}$ are the amplitudes of the fluorescence signals corresponding to each wavelength of integration. The electrical signals produced by the photodiode 25 are harmonic, as the high frequency components of the light source modulation are suppressed by the band-pass filter 27. The output voltage of the integrator 34 is proportional to the integral of the current flowing through a capacitor contained therein (not shown for clarity). In a preferred embodiment, the initial and final voltages are the lower $U_{lo}$ and the upper $U_{up}$ threshold of the trigger thus making the integration times $T_1$ and $T_2$ calculable by the equations $$T_1 = \frac{RC \cdot (U_{up} - U_{lo})}{n_1 \cdot I_1}, \quad T_2 = \frac{RC \cdot (U_{up} - U_{lo})}{n_2 \cdot I_2}. \quad (5, 6)$$

Here, RC is the integration constant of the integrator 34. In equations 3–6, the time intervals are assumed to be equal to a whole number of half waves—as the length of the integration time is usually more than $10^3$ times longer than the length of one halfwave, this does not introduce significant error. When the ratio of the intensities is calculated by $$\frac{I_{EI}}{I_{EI}} = K \frac{T_2}{T_1}, \quad (7)$$

the ratio of the time intervals ($T_2/T_1$) is proportional to the luminescence intensity ratio. The period of the square wave ($T_1+T_2$) is proportional to the concentration of the fluorophor. In a preferred embodiment, the ratio of the time intervals is evaluated using the timer 41 (digitizing the lengths of the intervals) and divider 42, in analyzer 40, for calculation of the ratio. Alternatively, the ratio of the time intervals may be evaluated by measurement of the DC component (duty ratio, DR) of the square wave. As DR=$T_1$/($T_1+T_2$), may be calculated by the equation $$\frac{T_2}{T_1} = \frac{1}{DR - 1}. \quad (8)$$

In accordance with these principles, a detailed description of a preferred embodiment of the analytic apparatus 1 performing an analyte measurement will now be discussed with reference to FIG. 1 so that one may better understand the present invention. The first light source 3 includes a high-brightness blue LED 4 having a maximum wavelength of 470 nm and 40 nm FWHM, and configured to excite a fluorescence emission from the sample. The second light source 6 includes a green LED having a maximum wavelength of 520 nm and 40 nm FWHM and configured to excite a fluorescence emission from the sample. For example, the blue LED 4, part number MBB51TAH-T (Micro Electronics Corp., Santa Clara, Calif.) with a luminous intensity of 4000 mcd, and the green LED 4, part number NSPG 500 (Nichia, Mounville, Pa.) with a luminous intensity of 5000 mcd, are used in the preferred embodiment. In the preferred embodiment, the dual-excitation indicator is carboxydichlorofluorescein-pH sensitive in solution.

In alternative embodiments, alternative dual excitation indicator dyes known in the art may be used to measure the pH in a sample. In such alternative embodiments, LEDs 4 used to match the excitation maxima of alternative dual excitation indicators are utilized as the first and second light sources to excite the fluorescence emissions from the sample having these aforementioned indicators, without departing from the scope of the invention.

It should further be understood that other dual-excitation indicators may be utilized to measure other analyte in a sample. In such cases, the sample may contain dual-excitation dyes that may be used to measure the analyte and alternative LEDs 4 used to match the excitation maxima of these alternative dual-excitation indicators will be utilized as the first and second light sources to excite the fluorescence and/or phosphorescence emissions from the sample.

The first light source 3 and the second light source 6 are sequentially enabled and disabled by the controller 30 so that the first and second light sources work completely out of phase. In other words, when the first light source 3 emits modulated light, the second light source 6 is off and when the second light source 6 is enabled thereby permitting the second light source 6 to emit modulated light, the first light source 3 is turned off.

The analyte measurement procedure begins with the first light source 3 turned on and the switches SW1 and SW2 in position I. The light from the first light source 3 passes through a band-pass filter 21 having a 470±10 nm bandwidth and excites fluorescence 13 in the sample contained in cuvette 24. The fluorescence emission 13 passes through the emission filter 23 having a 590±40 nm bandwidth and is detected by the photodiode 25 and amplified by the transimpedance amplifier 26 with an appropriate second amplification stage. In the case that other dual-excitation indicators are used to measure the analyte of the sample, the emission and the excitation filters are configured to the specifications of the excitation and emission maxima of the indicator used.

In a preferred embodiment, the LEDs 4 and 7 are driven using both a first voltage controlled current source 5 and a second voltage controlled current source 8. The LED current is modulated by a modulated voltage source 9 at frequency of 3 kHz. The LEDs are operated in pulse mode at a peak current of 60 mA—twice as much as the nominal rating. The total output optical power from the blue LED 4 is approximately 3.3 mW, and the power from the green LED 7 is approximately 1.4 mW.

In a preferred embodiment, the resulting electrical signal is passed through the second order, narrow band-pass active filter 27 with unity gain to remove the steady state components and diminish the low and high frequency noise. The center frequency of the pass-band is chosen to be equal to the modulation frequency of the LEDs 4 and 7. The output of the band-pass filter 27 is transmitted through the rectifier 31 for amplitude detection.

At this point in the measurement procedure, the switch SW2 is in position I allowing the output of the rectifier 31 to be transmitted to the integrator 34 wherein the first fluorescent signal corresponding to the fluorescent emission 13 is integrated. The output of the integrator 34 is connected to the trigger 35 with hysteresis which controls the switches SW1 and SW2. As the output of the amplitude detector 33 is positive, the output of the integrator 34 gradually increases, as can be seen in FIG. 2c, towards an upper threshold of the hysteresis trigger 35. When this upper threshold is reached, the hysteresis trigger 35 changes the positions of switches SW1 and SW2 to position II enabling the second light source 6 to illuminate the sample with modulated light and disabling the first light source 3 (turning the first light source 3 off).

The light from the second light source 6 passes through the excitation optical filter 22 and excites a second fluorescent emission 14 in the sample in cuvette 24. The fluorescence emission 14 passes through the emission optical filter 23 and is detected by the photodiode 25 and then amplified by the transimpedance amplifier 26. The resulting electrical signal is passed through the band-pass filter 27 to remove the steady state components and diminish the low and high frequency noise. The resulting electrical signal is transmitted through the rectifier 31 for amplitude detection.

At this point in the measurement procedure, the switch SW2 is in position II allowing the output of the rectifier 31 to be transmitted to the multiplier 32 wherein the amplitude of the electrical signal that corresponds to the second fluorescent emission 14 is multiplied by (−1), as can be seen in FIG. 2b. The output of the multiplier 32 is then transmitted to the integrator 34 wherein the fluorescent signal corresponding to the fluorescent emission 14 is integrated. As the output of the amplitude detector 33 is negative, the output voltage of the integrator 34 now gradually decreases, as can be seen in FIG. 2c, towards a lower threshold of the hysteresis trigger 35. When this lower threshold of the hysteresis trigger 35 is reached, the latter changes the switches SW1 and SW2 back to the position I thereby enabling the first light source 3 and disabling the multiplier 32. At this point, the illumination cycle is repeated.

As a result, on the output of the trigger 35 appears a square wave, as seen in FIG. 2d. Its duty ratio (T1/T2) is proportional to the luminescence intensity ratio. The period of the square wave (T1+T2) is proportional to the concentration of the fluorophor used. The duty ratio is measured by the analyzer 40 having the timer 41, for measuring the times T1 and T2 and the period of the square wave (T1+T2) output by the hysteresis trigger 35, and the divider 42 for producing the duty ratio.

Figure 3:
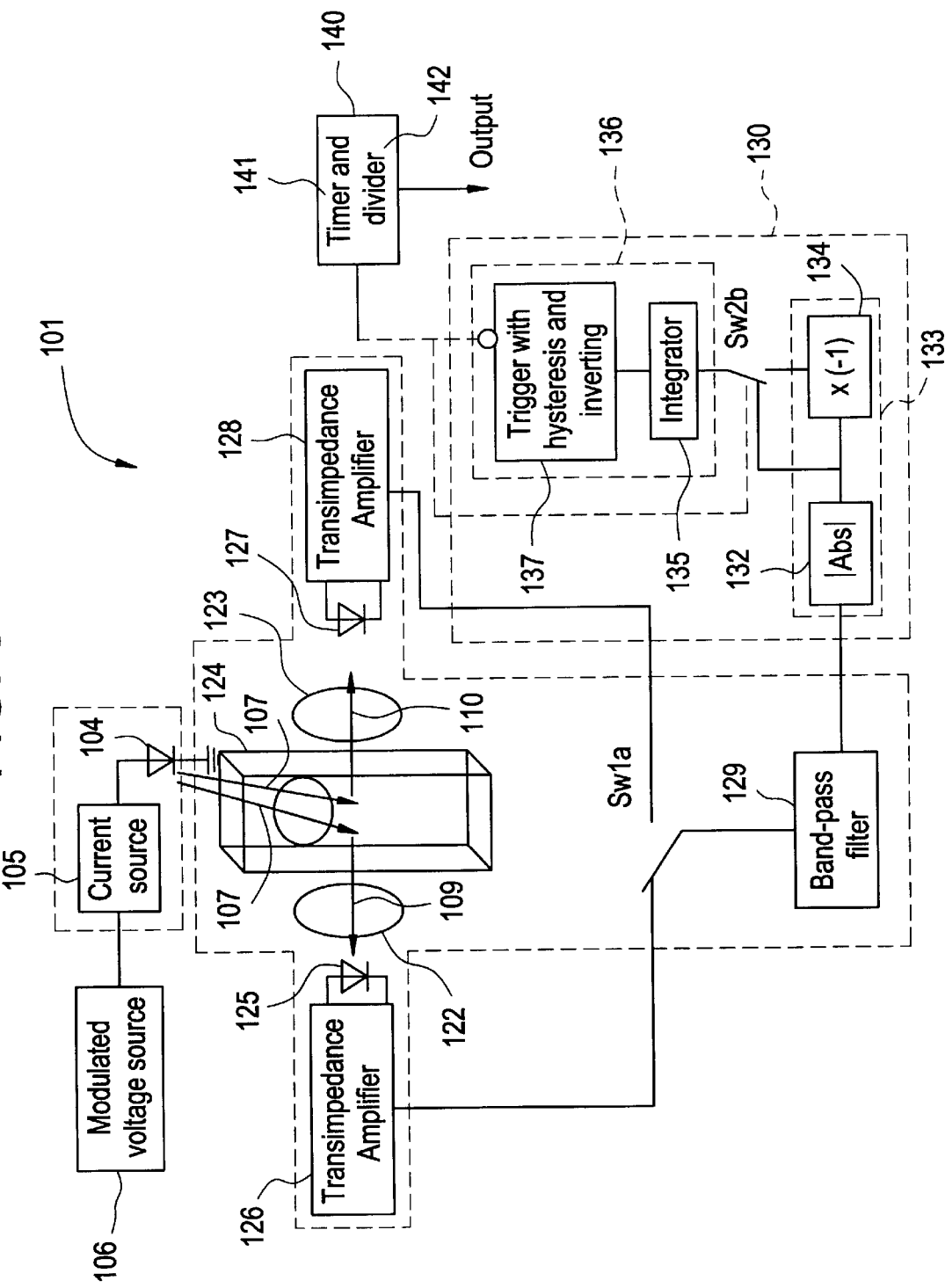
FIG. 3 is a second embodiment of the present invention.

Referring now to FIG. 3, a diagram of an analytic apparatus according to a second preferred embodiment of the present invention is shown. Analytic apparatus 101 includes a first light source 103, a controller 130, an emission detector 120, and an analyte analyzer 140 (analyzer) all interconnected using circuitry commonly known to those skilled in the art.

The light source 103 includes a LED 104 which produces excitation light 107 at a specific wavelength configured to excite fluorescence 109 and phosphorescence 110 from the dual-emission probe present within the sample disposed within a cuvette 124. LED 104 is coupled to a modulated voltage source 106 through a current source 105.

Emission detector 120 is configured to sequentially detect the fluorescence and phosphorescence emissions emitted from the sample and convert the aforementioned emissions into electrical signals corresponding to the luminescence intensity of the emissions. An analyzer 140 processes the electrical signals corresponding to the fluorescence and phosphorescence emissions and derives a fluorescence/phosphorescence duty ratio (described below) for at least one emission cycle of fluorescence and phosphorescence emissions. Analyzer 140 compares the calculated duty ratio with predetermined values to detect the concentration of the analyte in the sample.

As shown in FIG. 3, emission detector 120 (detector) preferably includes a translucent cuvette or a like container 124 having an internal dimension for holding a sample to be illuminated, and an excitation filter 121 for filtering the excitation light 107 produced by LED 104. It should be understood that the cuvette 24 is described to facilitate understanding the present invention, and does not form a part thereof. Any vessel performing the functions described herein may be used with the analytic apparatus 101 without departing from the scope of the present invention. A first photodetector 125 and a second photodetector 127 respectively convert the fluorescence emission 109 and the phosphorescence emission 110, emitted by the sample, to corresponding electrical signals. A first emission filter 122 disposed intermediate the sample and the first photodetector 125 is utilized to monitor the fluorescence emission 109. Similarly, a second emission filter 123 disposed intermediate the sample and the second photodetector 127 is utilized to monitor the phosphorescence emission 110.

With reference to FIG. 3, the electrical signals corresponding to the fluorescence and phosphorescence emissions 109 and 110 produced by the first and second photodetectors 125 and 127 are amplified by transimpedance amplifiers 126 and 128, respectively. Emission detector 120 further includes a band-pass filter 129 that both (i) removes steady-state components which originate from ambient light that enters the optical path of the fluorescent and phosphorescent emissions detected by the photodetectors 125 and 127, and (ii) diminishes the level of the low and high frequency noise, that accompanies the fluorescent and phosphorescent emissions, from the electrical signals produced by the photodetectors.

As can be seen from FIG. 3, the analytic apparatus 101 also includes a controller 130 that controls a detection cycle of the analytic apparatus 101 by sequentially enabling the first photodetector 125 and the second photodetector 127 in response to the electrical signals produced by the detector 120. Controller 130 further includes an amplitude detector 133 that takes the absolute value of the electrical signals produced by the emission detector 120 and assigns a sign to one of the electrical signals corresponding to the fluorescent 109 or phosphorescent 110 emissions. The controller further includes a voltage analyzer 136 that controls a pair of switches SW1a and SW2a, in response to the electrical signals output by the emission detector 120, that both enable the first photodetector 125 and the second photodetector 127 to operate in a sequential manner and direct the amplitude detector 133 to assign a negative value to the amplitude of one of the electrical signals corresponding to one of the fluorescent and phosphorescent emissions, respectively.

As can be seen from FIG. 3, the amplitude detector 133 includes a rectifier 132 and a multiplier 134. The rectifier 132 detects the amplitude of the electrical signals corresponding to the fluorescent and phosphorescent signals produced by the emission detector 120. One of the electrical signals corresponding to the fluorescent and phosphorescent emissions is transmitted to the multiplier 134 via the switch SW2a that is activated by the voltage analyzer 136. In a preferred embodiment, the amplitude of the electrical signal corresponding to the phosphorescence emission is assigned a negative value by transmitting that signal through the multiplier 134. Multiplier 134, in turn, converts the positive amplitude of the phosphorescence signal output by the rectifier 132 to a negative amplitude by multiplying the phosphorescence signal by (−1). Alternatively, the electrical signal corresponding to the fluorescence emission may be assigned a negative amplitude while the amplitude of the electrical signal corresponding to the phosphorescence signal may remain positive. The output of the amplitude detector is shown in FIG. 2b.

Referring to FIG. 3 again, voltage analyzer 136 includes an integrator 135 for integrating the electrical signals corresponding to the fluorescence and phosphorescence emissions output by the amplitude detector 133, and a hysteresis trigger 137 for directing the switches SW1a and SW2a in response to the output of the integrator 135, to enable one of the photodetectors and enable or disable the multiplier 134, respectively. As a result, the output of the hysteresis trigger 137 is a square wave, as can be seen in FIG. 2d. The time T1 illustrates the time that the first photodetector 125 is on during the emission cycle. The time T2 illustrates the time that the second photodetector 127 is on during the emission cycle. Analyzer 140 computes the output of the hysteresis trigger 137 to measure the hysteresis trigger duty ratio. Analyzer 140 includes a timer 141 and divider 142 for measuring the hysteresis trigger duty ratio, as described above.

In accordance with these principles, a detailed description of a preferred embodiment of the analytic apparatus 101 performing an analyte measurement will now be discussed with reference to FIG. 3 so that one may better understand the present invention. The light source 103 includes a blue LED 104, part number MBB51TAH-T (Microelectronics, Santa, Clara, Calif.) having a maximum wavelength of 470 nm is used. LEDs that cover part of the light spectrum needed to excite the particular dual emissive dye may be utilized.

The sample containing the analyte to be measured is placed in a cuvette 124 equipped with a screw top, a septum, and inlet and outlet lines (not shown) to allow gas flow. In a preferred embodiment, [(1,2-bis(diphenylphosphino)ethane)Pt$\{S_2C_2(CH_2CH_2$—N-2-pyridinium)$\}$][BPh$_4$]—oxygen sensitive in film—is used as the dual-emissive dye. This luminescent dye is immobilized at 0.3% by weight in CA/TEC and cast in a 0.5 mm thick film. The film is trimmed and mounted to a quartz cuvette insert (not shown) with Super 77 spray adhesive (3M, Saint Paul, Minn.) and disposed inside the cuvette 124. In alternative embodiments, alternative dual emission indicator dyes may be used to measure the oxygen in the sample. In such alternative embodiments, the appropriate LED used to excite fluorescence and/or phosphorescence from the particular dye are used as the light source. In such alternative embodiments, other analyte in the sample may be measured by utilizing dual emission dyes that are sensitive to the analyte to be measured. In these alternative embodiments, the appropriate LED may be used to excite fluorescence and phosphorescence or two different fluorescence from the sample in the manner described above, without departing from the scope of the invention.

The modulated light emitted from the LED ($f_{mod}$=1.5 kHZ) is directed to the sample through a 470±30 nm band-pass filter mounted on the cuvette wall. The excitation light emitted by the blue LED 104 causes the dual-emissive probe to sequentially emit fluorescence and phosphorescence due to the singlet and triplet emissions (discussed above). The fluorescence and phosphorescence emissions are monitored through 570±40 nm and 680±22 nm band-pass filters, respectively. The corresponding light intensities are detected by two large active-area (13 mm$^2$) PIN-photodiode detectors 125 and 127. The electrical signals, corresponding to the fluorescence and phosphorescence, are amplified and passed through a band-pass filter 129 to both (i) reject steady-state components, which originate from ambient light entering the optical path between the sample and the photodetectors, and (ii) diminish the levels of low and high frequency noise. After amplitude detection and sign assignment, the signals are serially fed through the switch SW2a to the integrator.

When SW1a and SW2a are in position I, the fluorescent signal is integrated. As it is positive, the output voltage of the integrator 135 gradually increases to the upper threshold of the hysteresis trigger 137. This switches SW1a and SW2a switch to position 11 where the phosphorescent signal is integrated. As it is negative (discussed above), the integrator's 135 output voltage now gradually decreases. When the output voltage reaches the lower threshold of the hysteresis trigger 137, SW1a and SW2a switch back to position I and the process is repeated.

The above-described techniques may also be applied to the measurement of various other kinds of analyte in a sample. In addition, it is to be understood that various other types of measurements may be achieved with the present invention. Such measurements include the measurement of the ratio of two different samples.

It should be understood that other dual-excitation probes and dual-emission probes, besides the several described above, may also be appropriate for measuring the oxygen, pH, $Ca^{2+}$, $Mg^{2+}$, $Zn^{2+}$, heavy metals and/or transmembrane potentials concentration of a sample.

It will therefore be seen that the foregoing represents a highly advantageous approach to analyte measurement in a sample. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

For example, alternative light sources may be used to illuminate the sample such as laser diodes, lasers, incandescent lamps, and semiconductor light sources (to name a few) without departing from the novel spirit and scope of the present invention. Moreover, excitation light from the ultraviolet to the visible range may be used to irradiate the sample and the apparatus of an alternative embodiment may be configured to analyze emissions from the visible to the infrared range to determine the concentration of analytes present in a sample without departing from the novel spirit and scope of the present invention.

We claim:

1. An apparatus for measuring an analytic concentration of a sample comprising:
    a sample containing a dual wavelength-absorbing luminescent compound or a dual wavelength-emitting luminescent compound,
    a first light source producing a first light having a first wavelength to be directed at the sample to produce a first emission from the sample;
    a second light source producing a second light having a second wavelength to be directed at the sample to produce a second emission from the sample;
    a detector for detecting said first emission and said second emission emitted from the sample;
    a controller coupled to said first light source, said second light source and said detector for alternately switching between said first light source and said second light source so that only one light source is directing light at the sample; and
    an analyzer coupled to said controller, wherein said analyzer produces a duty ratio which is used to determine the analytic concentration of the sample.

2. The apparatus of claim 1, wherein said first light source comprises a first LED and said second light source comprises a second LED.

3. The apparatus of claim 1, wherein said controller comprises a rectifier for rectifying said electrical signals produced by said detector and a multiplier for multiplying the electrical signals corresponding to one of either said first emission or said second emission.

4. The apparatus of claim 3, wherein said controller means further comprises a first switch and a second switch, an integrator for integrating said electrical signals output by said detector and a hysteresis trigger to direct both said first switch and said second switch to synchronously switch between a plurality of modes, switching from a first mode to a second mode in response to an integrator output reaching a first level and switching from a second mode to a first mode in response to said integrator output reaching a second level.

5. The apparatus of claim 1, wherein said detector comprises a first excitation filter for filtering said first light, a second excitation filter for filtering said second light, a photodetector for converting said first emission and said second emission emitted by the sample to corresponding electrical signals, an emission filter disposed intermediate the sample and said photodetector for monitoring said first emission and said second emission, and a band-pass filter for removing steady-state components and noise from said electrical signals produced by said photodetector.

6. The apparatus of claim 1, wherein said analyzer comprises a timer for measuring a time 1 and a time 2 to produce a square wave period equal to the sum of said time 1 and said time 2, which is proportional to a concentration of fluorophor used in the sample.

7. The apparatus of claim 6, wherein said analyzer comprises a divider for dividing said time 1 by said time 2 to produce said duty ratio, which is proportional to a luminescence intensity ratio of said first emission and said second emission.

8. The apparatus of claim 1, wherein the sample comprises a dual-emissive probe that emits said first emission when illuminated by said first light and said second emission when illuminated by said second light, said first emission is fluorescence and said second emission is fluorescence.

9. The apparatus of claim 1, wherein the sample comprises a dual-emissive probe that emits said first emission when illuminated by said first light and said second emission when illuminated by said second light, said first emission is phosphorescence and said second emission is phosphorescence.

10. An apparatus for measuring an analytic concentration of a sample comprising:
    a sample containing a dual wavelength-absorbing luminescent compound or a dual wavelength-emitting luminescent compound, a light source producing a light to be directed at the sample to produce a first emission and a second emission from the sample;

a detector for detecting said first emission and said second emission emitted from the sample;

a controller coupled to said light source and said detector, wherein said controller operates a first switch and a second switch in response to said detector; and an analyzer coupled to said controller for producing a duty ratio which is used to determine the analytic concentration of the sample.

11. The apparatus of claim 10, wherein said light source comprises a LED.

12. The apparatus of claim 10, wherein said detector comprises a first photodetector for producing electrical signals proportional to the intensity of said first emission and a second photodetector for producing electrical signals proportional to the intensity of said second emission.

13. The apparatus of claim 12, wherein said controller comprises a rectifier for rectifying said electrical signals produced by said first and second photodetectors and a multiplier for multiplying said electrical signals corresponding to one of either said first emission or said second emission.

14. The apparatus of claim 13, wherein said controller further comprises an integrator for integrating said electrical signals output by said detector, and a hysteresis trigger for directing both said first switch and said second switch to synchronously switch between a plurality of modes.

15. The apparatus of claim 12, wherein said detector further comprises an excitation filter for filtering said light, a first emission filter disposed intermediate the sample and said first photodetector for monitoring said first emission, a second emission filter disposed intermediate the sample and said second photodetector for monitoring said second emission, and a band-pass filter for removing steady-state components and noise from said electrical signals produced by said first and second photodetectors.

16. The apparatus of claim 10, wherein said analyzer comprises a timer for measuring a time 1 and a time 2 to produce a square wave period equal to the sum of said time 1 and said time 2, which is proportional to a concentration of fluorophor used in the sample.

17. The apparatus of claim 16, wherein said analyzer comprises a divider for dividing said time 1 by said time 2 to produce said duty ratio, which is proportional to a luminescence intensity ratio of said first emission and said second emission.

18. The apparatus of claim 10, wherein the sample comprises a dual-emissive probe that emits fluorescence and phosphorescence when illuminated by said light.

19. The apparatus of claim 10, wherein the sample comprises a dual-emissive probe that emits fluorescence and fluorescence when illuminated by said light.

20. The apparatus of claim 10, wherein the sample comprises a dual-emissive probe that emits phosphorescence and phosphorescence when illuminated by said light.

21. A method for measuring an analytic concentration of a sample, comprising the steps of:

directing a first light source having a first wavelength at a sample containing a dual wavelength-absorbing luminescent compound or a dual wavelength-emitting luminescent compound to generate a first emission from the sample;

directing a second light source having a second wavelength at the sample to a second emission from the sample;

alternatively switching between the first light source and the second light source so that only one light source is directing light at the sample;

detecting the first emission and the second emission emitted from the sample; and generating a duty ratio from the first emission and the second emission to determine the analytic concentration of the sample.

22. The method of claim 21, further comprising the step of generating electrical signals proportional to the intensity of the first emission and the second emission.

23. The method of claim 21, wherein the step of switching between the first light source and the second light source comprises the step of disabling one light source while enabling the other light source to operate the lights in a sequential manner.

24. The method of claim 22, wherein the step of alternatively switching comprises the steps of rectifying the electrical signals corresponding to one of either the first emission or the second emission, and rectifying and multiplying by a constant the electrical signals corresponding to the other of either the first emission or the second emission.

25. The method of claim 24, wherein the step of alternatively switching further comprises the steps of integrating the electrical signals corresponding to the first emission and the second emission, and switching between the first light source and the second light source in response to the integrated electrical signals reaching a first level and a second level.

26. The method of claim 25, wherein the generating step comprises measuring a time 1 and time 2 wherein the time 1 represents a time that the first light source is on for part of an illumination cycle and the time 2 represents a time that the second light source is on for the remainder of the illumination cycle.

27. The method of claim 26, wherein the generating step further comprises adding the time 1 to the time 2 to determine a concentration of fluorophor used in the sample and dividing the time 1 by the time 2 to produce the duty ratio.

* * * * *